United States Patent [19]
Siman

[11] Patent Number: 5,871,712
[45] Date of Patent: Feb. 16, 1999

[54] METHODS FOR DETECTING CALPAIN ACTIVATION AND IDENTIFYING CALPAIN INHIBITORS

[75] Inventor: Robert Siman, Wilmington, Del.

[73] Assignee: Cephalon, Inc., West Chester, Pa.

[21] Appl. No.: 592,098

[22] Filed: Jan. 26, 1996

Related U.S. Application Data

[62] Division of Ser. No. 217,989, Mar. 25, 1994, Pat. No. 5,536,639.
[51] Int. Cl.$^6$ ..................................................... G01N 33/53
[52] U.S. Cl. ............................ 424/9.1; 435/71; 435/7.21
[58] Field of Search .................................... 435/7.1, 7.21, 435/7.92, 7.93, 7.94, 7.95, 70.21, 240.27; 424/9.1, 9.2; 436/518, 528, 530, 531, 548

[56] References Cited

U.S. PATENT DOCUMENTS

| | | |
|---|---|---|
| 5,118,606 | 6/1992 | Lynch et al. . |
| 5,444,042 | 8/1995 | Bartus et al. . |

FOREIGN PATENT DOCUMENTS

| | | |
|---|---|---|
| WO 92/01935 | 2/1992 | WIPO . |
| WO 92/11850 | 7/1992 | WIPO . |

OTHER PUBLICATIONS

Baudry et al., "Micromolar Calcium Stimulates Proteolysis and Glutamate Binding in Rat Brain Synaptic Membranes," Science 212:937–38 (1981).
Davis et al., "Brain Spectrin," J. Biol. Chem. 258:7757–66 (1983).
Ferrell, et al., "Thrombin Stimulates the Activities of Multiple Previously Unidentified Protein Kinases in Platelets," J. Biol. Chem. 264:20723–29 (1989).
Harlowe et al., *Antibodies, a Laboratory Manual*, by Cold Spring Harbor Laboratories MA, pp. 72–137 (1988).
Harris et al., "The Calmodulin–binding Site in ≃–Fodrin Is Near the Calcium–dependent Protease–I Cleavage Site," J. Biol. Chem. 263:15754–61 (1988).
Lee et al., "Inhibition of proteolysis protects hippocampal neurons from *ischemia*," Proc. Natl. Acad. Sci. 88:7233–37 (1991).
Nadler, et al., "Use of Excitatory Amino Acids to Make Axon–Sparing Lesions of Hypothalamus," Meth. Enzymol. 103:393–400 (1983).
Pacella et al., *Molecular Immunology* 29(5):521–527 (1983).
Peterson, "Increased spectrin proteolysis in fibroblasts from aged and Alzheimer donors," *Neuroscience Letters* 121:239–243 (1991).
Roberts–Lewis et al., "Spectrin Proteolysis in the Hippocampus: A Biochemical Marker for Neuronal Injury and Neuroprotection," Ann. N.Y. Acad. Sci., 679:78–86 (1993).
Schanne et al., "Calcium Dependence of Toxic Cell Death: A Final Common Pathway," Science 206:700–702 (1979).
Seubert et al., "Calmodulin Stimulates the Degradation of Brain Spectrin by Calpain," Synapse 1:20–24 (1987).
Seubert et al., "*Ischemia* triggers NMDA receptor—linked cytoskeletal proteolysis in *hippocampus*," Brain Res. 492:366–70 (1989).
Siman et al., "Expression of β–Amyloid Precursor Protein in Reactive Astrocytes following Neuronal Damage," Neuron 3:275–85 (1989).
Siman et al., "Calpain I Activation is Specifically Related to Excitatory Amino Acid Induction of Hippocampal Damage," J. Neurosci. 9:1579–90 (1989).
Siman, "Role of Calpain I in Excitatory Amino Acid–Induced Degenerative Structural Changes," Neurotoxicity of Excitatory Amino Acids, pp. 145–161 (1990).
Siman et al., "Purification from Synaptosomal Plasma Membranes of Calpain I, a Thiol Protease Activated by Micromolar Calcium Concentrations," J. Neurochem. 41:950–56 (1983).
Siman et al., "Excitatory Amino Acids Activate Calpain I and Induce Structural Protein Breakdown in Vivo," Neuron 1:279–87 (1988).
Pacella et al., "Induction of Fibrin–Specific Antibodies By Immunization with Synthetic Peptides That Correspond to Amino Termini of Thrombin Cleavage Sites," *Molecular Immunology* 20(5):521–527 (1983).

Saido et al., "Spatial Resolution of Fodrin Proteolysis in Postichemic Brain," *J. Biol. Chem.* 268(33):25239–25243 (1993).

Siman et al., "Brain fodrin: Substrate for calpain I, and endogenous calcium–activated protease," *Proc. Natl. Acad. Sci. USA* 81:3572–3576 (1984).

*Primary Examiner*—Paula K. Hutzell
*Assistant Examiner*—Patricia A. Duffy
*Attorney, Agent, or Firm*—Fish & Richardson P.C.

[57] ABSTRACT

The invention provides methods for detecting calpain activation by measuring levels of calpain-generated spectrin BDPs using antibodies that specifically bind to these spectrin BDPs, but not intact spectrin, or spectrin BDPs generated by other proteases. Also included in the invention are kits for diagnosing diseases associated with increased levels of calpain activation, and methods for screening for effective therapeutics for these diseases.

6 Claims, 9 Drawing Sheets

METHODS FOR DETECTING CALPAIN ACTIVATION AND IDENTIFYING CALPAIN INHIBITORS

This is a divisional of application Ser. No. 08/217,989, filed Mar. 25, 1994, now U.S. Pat. No. 5,536,639.

BACKGROUND OF THE INVENTION

This invention relates to diagnosis and therapy of neurodegenerative conditions.

Calcium concentrations inside nerve cells are normally tightly regulated to levels (~50–100 nM) several orders of magnitude lower than calcium levels in extracellular fluids (1–2 mM). Under pathological states of injury or disease, however, intraneuronal calcium concentrations increase, leading to degeneration from calcium overload (Schanne et al., Science 206:700–702, 1979). A toxic rise in calcium content stimulates a number of calcium-dependent processes, including the activation of lipases, nucleases, and proteases. The relative contributions of these various calcium-dependent enzymes to the nerve cell death triggered by calcium overload are not established, but a number of indirect studies point to the importance of activation of a calcium-dependent protease, known as calpain I or $\mu$-calpain, in neurodegeneration (Siman et al., Neuron 1:279–287, 1988; Seubert et al., Brain Res. 492:366–370, 1989; Siman et al., J. Neurosci. 9:1579–1590, 1989; Siman, Neurotoxicity of Excitatory Amino Acids (Guidotti, A., ed.) Raven, New York, pp. 145–161, 1990; Lee et al., Proc. Natl. Acad. Sci. U.S.A. 88:7233–7237, 1991, and references therein).

The cytoskeleton is a mesh-like filamentous structure that maintains the structural integrity of the cell. Spectrin (also known as fodrin) is a major component of the cytoskeleton in many cell types, including neurons. Calpain-mediated proteolysis of spectrin produces a single cleavage at an identified site in the $\alpha$-subunit that splits the $\alpha$-subunit approximately in half (Harris et al., J. Biol. Chem. 263:15754–15761, 1988). Calpain activation and elevated levels of spectrin breakdown products (BDPs) have been associated with several neurodegenerative conditions, including those caused by Alzheimer's Disease, Parkinson's Disease, muscular dystrophy, Pick's disease, subarachnoid hemorrhage, HIV-induced neuropathy, stroke, hypoxia, ischemia, lesions, and exposure to toxins.

Lynch et al. (U.S. Pat. No. 5,118,606) describe methods for detecting cellular degeneration using antibodies to intact spectrin to detect spectrin breakdown products. Bartus et al. (WO 92/11850) describe several classes of calpain inhibitors and methods for identifying calpain inhibitors in which an antibody to intact spectrin is used in Western blot analysis to detect spectrin breakdown products.

SUMMARY OF THE INVENTION

The invention features antibodies that can be used to detect calpain activation by recognizing calpain-generated spectrin breakdown products (BDPs), but not intact spectrin. Calpain-generated spectrin BDPs are specifically enriched in biological samples from subjects that have experienced a non-pathological cellular insult or a pathological disease, relative to control subjects which have not experienced these conditions. Thus, detection of calpain activation by measuring the level of calpain-generated spectrin BDPs is useful for diagnosing these conditions.

Accordingly, in one aspect, the invention features a method of detecting calpain activation by measuring the level of calpain-generated spectrin BDPs in a biological sample. The method involves contacting the sample with an antibody that specifically binds to a peptide having the amino acid sequence of either SEQ ID NO: 1 or SEQ ID NO: 2, but not intact spectrin, and determining the level of the antibody bound to the sample relative to a control in an immunoassay as a measure of the level of spectrin BDPs in the sample. The control can be a comparable sample (e.g., the same volume of blood) from an unaffected individual, or can be a preparation containing an amount of calpain-generated spectrin BDPs equivalent to that which would be in a comparable sample from an unaffected individual. Suitable antibodies include polyclonal antibodies, i.e., those capable of generation by immunization, and monoclonal antibodies. In a preferred embodiment, the antibody is selected from a group consisting of Ab36, Ab37, Ab38, Ab39, Ab40, and Ab41.

Measurement of calpain-generated spectrin BDP levels can be carried out by the use of an immunoassay which allows detection of binding between spectrin BDPs and a spectrin BDP-specific antibody (as used herein, the term "spectrin BDP-specific antibody" refers to an antibody that recognizes calpain-generated spectrin BDPs, but not intact spectrin). The amount of bound antibody can be determined by analysis of enzymatic, chromogenic, radioactive, fluorescent, or luminescent labels that are attached to either the antibody which binds to the spectrin BDPs or to a secondary antibody which recognizes the antibody which binds to the spectrin BDPs. Immunoassays which may be used in the invention include, but are not limited to, ELISA, cell-based ELISA, filter-binding ELISA, inhibition ELISA, Western blots, immunoprecipitation, slot or dot blot assays, immunostaining, RIA, scintillation proximity assays, fluorescent immunoassays using antibody conjugates or antigen conjugates of fluorescent substances such as fluorescein or rhodamine, Ouchterlony double diffusion analysis, and immunoassays employing an avidin-biotin or a streptavidin-biotin detection system.

Spectrin breakdown products have been detected in a number of tissues and biological fluids including blood, cerebrospinal fluid (CSF), blood platelets, submandibular gland, brush border, testes, thymus, skeletal muscle, heart muscle, lung, liver, spleen, adrenal gland, kidney, and brain. Preferred biological samples for diagnosing neurodegenerative conditions by determining the level of calpain-generated spectrin breakdown products include, but are not limited to CSF, amniotic fluid, blood, and components of blood.

The methods of the invention can be used to diagnose a mammal, such as a human, who has or is at risk of developing a pathological condition, and an increased level of calpain-generated spectrin BDPs. In a preferred embodiment, the pathological condition affects the nervous system and may be selected from, but is not limited to, a group consisting of Alzheimer's Disease, Parkinson's Disease, muscular dystrophy, multiple infarction dementia, intraventricular hemorrhage, Pick's disease, subarachnoid hemorrhage, HIV-induced neuropathy, stroke, and retinal disease.

The methods of the invention can also be used to diagnose a non-pathological cellular insult in a mammal that may be selected from, but is not limited to, the group consisting of trauma, hypoxia, anoxia, ischemia, spinal trauma, head trauma, lesions, and exposure to toxins. In a preferred embodiment the cellular insult is to the nervous system.

The invention also features a method for in situ detection of sites of calpain activation in a subject. In this method, antibodies specific for calpain-generated spectrin BDPs are administered to a subject using methods and dosages determined appropriate by one skilled in the art. The locations of the antibodies bound to spectrin BDPs in the subject can be determined by imaging techniques known in the art, and can be compared to the pattern of antibody localization observed in a control subject that has not experienced a cellular insult or pathological condition resulting in calpain activation.

In another aspect, the invention features an antibody that specifically binds to a peptide having the amino acid sequence of either SEQ ID NO: 1 or SEQ ID NO: 2. Antibodies included in the invention can be monoclonal or polyclonal. The invention also features substantially pure peptides having the amino acid sequences of SEQ ID NO: 1 and SEQ ID NO: 2. These peptides can be used in methods of generating antibodies that specifically recognize them, in which a mammal is immunized with the appropriate peptide or peptide conjugate. Methods of generating both monoclonal and polyclonal antibodies that recognize these peptides are included in the invention.

The invention also features a kit for in vitro determination of the level of calpain-generated spectrin BDPs in a sample. A kit for detecting spectrin BDPs may include: (1) a primary antibody capable of binding to spectrin BDPs (but not intact spectrin); (2) a secondary antibody conjugated to a signal-producing label, the secondary antibody being one that binds to the primary antibody; and (3) a signal producing tertiary reagent capable of recognizing a tagged secondary antibody.

Another kit that is useful for detection of calpain-generated spectrin BDPs and a part of the invention includes (1) a primary antibody capable of binding to spectrin BDPs (but not intact spectrin); and (2) a secondary antibody conjugated to a signal-producing label, the secondary antibody also being a spectrin BDP-specific antibody, but one that binds to a site different from (i.e., spaced from) that to which the first antibody binds. This kit is most suitable for carrying out a two-antibody sandwich immunoassay, e.g., a two-antibody sandwich ELISA, and preferably employs monoclonal antibodies.

In each of the above-described assay kits, the signal-producing label linked to the secondary antibody may be, but is not limited to, an enzyme (e.g., horseradish peroxidase or alkaline phosphatase). Preferably, both the enzyme and the substrate are provided in the kit. An uncoated support can also be included in the kit onto which the sample to be assayed (in the first kit described above) or the first antibody (in the second kit described above) can be immobilized by the user. The kit may also include purified spectrin BDPs to be used as standards. In preferred embodiments, the above-described kits contain an antibody selected from the group consisting of Ab36, Ab37, Ab38, Ab39, Ab40, and Ab41.

In another aspect, the invention features a biochemical method for determining the ability of a candidate compound to inhibit calpain activity. In this method, purified spectrin is incubated with calpain in the presence and absence of the candidate compound under conditions in which calpain is activated, and the level of calpain-generated spectrin BDPs formed is measured in an immunoassay using a spectrin BDP-specific antibody. A compound tests positive if the amount of spectrin BDPs present in the sample containing the inhibitor is less than that present in the sample lacking the inhibitor.

The invention also features a method for measuring the ability of a candidate compound to decrease calpain activity in a cell. In this method, a cell that expresses calpain and spectrin is exposed to, or cultured in the presence and absence of, the candidate compound under conditions in which calpain is activated in the cell, and the level of calpain-generated spectrin BDPs formed is measured in an immunoassay using a spectrin BDP-specific antibody. A compound tests positive if the amount of calpain-generated spectrin BDPs present in the sample prepared from the cells that were exposed to or cultured in the presence of the inhibitor is less than that present in the sample from the control cells.

In a final aspect, the invention features a method for measuring the ability of a candidate compound to decrease the activity of calpain in a mammal. In this method, a candidate compound is administered to a mammal, such as a gerbil, mouse, or rat, and the level of calpain activity is determined using the immunoassays described above. A compound tests positive if the amount of spectrin BDPs present in a sample taken from the animal to which the inhibitor had been administered is less than that present in an equivalent sample from an untreated animal.

As used herein, the term "substantially pure" describes a compound, e.g., a protein or polypeptide, e.g., peptides having the amino acid sequence of either SEQ ID NO: 1 or SEQ ID NO: 2, which has been separated from other components which naturally accompany it. Typically, a compound is substantially pure when at least 75%, more preferably at least 90%, and most preferably at least 99%, of the total material (by volume, by wet or dry weight, or by mole percent or mole fraction) in a sample is the compound of interest. Purity can be measured by any appropriate method, e.g., in the case of polypeptides by column chromatography, polyacrylamide gel electrophoresis, or HPLC analysis. A compound, e.g., a protein, is also substantially purified when it is essentially free of naturally associated components or when it is separated from the native contaminants which accompany it in its natural state.

The terms "specifically binds" and "specifically recognizes", as used herein, describe antibodies (e.g., Ab36, Ab37, Ab38, Ab39, Ab40, or Ab41) that recognize and bind spectrin BDPs, but do not substantially recognize and bind other molecules (including intact spectrin) in a sample, e.g., a biological sample, which may naturally include spectrin BDPS. The antibodies defined herein can be either monoclonal or polyclonal.

An advantageous feature of the antibodies and methods of the invention is that they allow spectrin BDPs to be distinguished from intact spectrin without requiring their fractionation, as the antibodies are specific for calpain-generated spectrin BDPs. The method also distinguishes calpain-generated spectrin BDPs from those produced by spectrin cleavage by other proteases, and so they are specific for activated calpain. This represents a significant improvement over the methods of Lynch et al. (U.S. Pat. No. 5,118,606) which require spectrin breakdown products to be physically separated from intact spectrin in order to be detected, e.g., by gel electrophoresis followed by Western blot analysis, or by differential precipitation.

This difference is very significant, as fractionating samples, as required in Western blot analysis, is considerably more expensive, cumbersome, and time consuming than the methods of the present invention, as well as requiring greater technical expertise. The present invention allows spectrin and spectrin BDPs to be distinguished by a more simple, inexpensive assay, such as an ELISA, which allows the processing of multiple samples in a short time. Thus, the present invention provides greatly improved methods for detecting spectrin BDPs.

Other features and advantages of the invention will become apparent from the following detailed description, the drawings, and from the claims.

DETAILED DESCRIPTION

The drawings are first described.

Drawings

FIGS. 4A–4G are representative photographs of immunohistochemical analysis of sagittal sections of control, untreated gerbil brain (FIG. 4A) or brains of gerbils subjected to 5 minutes of global cerebral ischemia (FIGS. 4B–4F): (FIG. 4B) 30 minutes post-ischemia; (FIG. 4C) 1 day post-ischemia; (FIG. 4D) 2 days post-ischemia; (FIG. 4E) 10 days post-ischemia; (FIG. 4F) a higher power view of area CA1 of the hippocampus, 2 days post-ischemia; (FIG. 4G) same as in (FIG. 4F), except that the antibody to calpain-degraded spectrin was preabsorbed with peptide immunogen. PC-parietal cortex; PC-frontal cortex; TT-tenia tecta; Pir-piriform cortex; S-striatum; VT-ventral thalamus; H-hippocampus; CA1-hippocampal CA1 region. Scale bar in (FIGS. 4A–4E) is 1 mm and is 60 $\mu$m in (FIGS. 4F–4G). Sections were stained with Ab37.

FIGS. 5A–5B are representative photographs of immunohistochemical analysis of hippocampal and cerebral cortical neurons from gerbils subjected to 5 minutes of ischemia. (FIG. 5A) Hippocampal CA2/3 border, 30 minutes post-ischemia. Asterisk denotes a pyramidal cell body. Arrowheads denote immunoreactive basal dendrites, while the arrows denote labeled apical dendrites. (FIG. 5B) Parietal cortex, layer V, 30 minutes post-ischemia. Scale bar is 10 $\mu$m.

FIGS. 6A–6C are representative photographs of immunohistochemical analysis of sagittal sections of gerbil brain prepared under the following conditions: (FIG. 6A) hippocampus, 1 minute of ischemia, 1 day post-insult; (FIG. 6B) 5 minutes of ischemia, 3 days post-insult; (FIG. 6C) 10 minutes of ischemia, 3 days post-insult.

FIGS. 7A–7E are representative photographs of immunohistochemical analysis of gerbil brain subjected to 5 minutes of cerebral ischemia. (FIG. 7A) CA1 region of the hippocampus, 2 days post-ischemia; (FIG. 7B) same as (FIG. 7A), except MK-801 was administered at time of ischemia; (FIGS. 7C–7D) layers I–III of the parietal cortex, 1 day post-ischemia; (FIG. 7E) thalamus, 1 day post-ischemia; (FIGS. 7C and 7E) control; (FIG. 7D) MK-801. Scale bars are 100 $\mu$m (FIGS. 7A–7B); 50 $\mu$m (FIGS. 7C–7D); 25 $\mu$m (FIG. 7E).

Antibodies

The present invention provides methods for detecting spectrin BDPs in a sample using antibodies that recognize spectrin BDPs generated by activated calpain, but not intact spectrin, or the spectrin BDPs generated by other proteases. As increased levels of calpain activation have been associated with several neurodegenerative conditions, the antibodies of the invention can be used in methods to diagnose these conditions, and in methods for identifying calpain inhibitors. The antibodies of the invention can be used in methods for detecting spectrin BDPs, such as an ELISA, that are significantly more simple, inexpensive, rapid, and less cumbersome compared to methods in which fractionation is required, such as Western blot analysis.

Antibodies that recognize calpain-generated spectrin breakdown products, but not intact spectrin, can be made by using peptides which correspond to either the COOH-terminus of the NH2-terminal calpain-generated spectrin fragment (CQQQEVY; SEQ ID NO: 1), or to the NH2-terminus of the COOH-terminal calpain-generated spectrin fragment (GMMPRDGC; SEQ ID NO: 2) as immunogens. These peptides can be generated by standard methods known in the art. Other peptide immunogens included in the invention are those which contain NH2-terminal extensions of SEQ ID NO: 1, and COOH-terminal extensions of SEQ ID NO: 2. Other protein or peptide antigens which, regardless of their origin, length, or degree of exact homology with naturally occurring spectrin breakdown products, lead to the production of antibodies which bind specifically to the calpain-cleaved spectrin BDPs and not intact spectrin, may also be useful in the methods of the invention.

The peptide antigens described above may be used to generate either monoclonal or polyclonal antibodies using standard methods in the art (for example, see Sambrook et al., Molecular Cloning, a Laboratory Manual, 2nd edn., Cold Spring Harbor Laboratory Press, Cold Spring Harbor, N.Y., 1989; Harlow et al., Antibodies, A Laboratory Manual, Cold Spring Harbor Laboratory Press, Cold Spring Harbor, N.Y., 1988).

In order to identify antibodies that are useful in the methods of the invention, the reactivities of the antibodies to intact and calpain-cleaved spectrin must be compared. Any source of spectrin and spectrin breakdown products can be used. For example, spectrin can be purified as described by Davis et al. (Davis et al., J. Biol. Chem. 258:7757–7766, 1983) and incubated under appropriate conditions (100 $\mu$M CaCl$_2$, 20 mM Tris-HCl (pH 7.5), 5 mM $\beta$-mercaptoethanol ($\beta$ME), 150 mM NaCl, at 30° C.) in the presence and absence of calpain (~3 $\mu$g/ml; purified by the method of Seubert et al., Synapse 1:20–24, 1987). Alternatively, tissue samples (e.g., brain homogenates or blood) from an animal in which ischemia has been induced can be compared with a similar tissue sample taken from a control, untreated animal. In addition, extracts from cells in which calpain has been activated can be compared to control extracts (see below).

The reactivities of the antibodies to spectrin and spectrin breakdown products can be compared in any of a number of immunoassays that are well known in the art. For example, modified enzyme immunoassays, such as ELISA, filter-binding ELISA, Western blots, immunoprecipitation, slot blot assays, or dot blot assays can be used. Also included in the invention are any of the known modifications of radioimmunoassays, fluorescent immunoassays, Ouchterlony double diffusion analysis, and immunoassays employing an avidin-biotin or streptavidin-biotin detection system.

Use of Antibodies for Diagnosis of Neurodegenerative Conditions

Calpain activation is thought be an early event in the process of neuronal degeneration, occurring prior to overt neuronal disintegration. Thus, detection of calpain-generated spectrin breakdown products is an advantageous method for the early detection of neurodegenerative conditions, potentially prior to the onset of pathological symptoms.

Antibodies found to be useful in the immunoassays described above can be used in methods to diagnose pathological conditions of the nervous system including, but not limited to, Alzheimer's Disease, Parkinson's Disease, muscular dystrophy, multiple infarction dementia, intraventricular hemorrhage, Pick's disease, subarachnoid hemorrhage, HIV-induced neuropathy, stroke, and retinal disease, as well as non-pathological cellular insults which affect the nervous system including trauma, hypoxia, anoxia, ischemia, head trauma, spine trauma, lesions, and exposure to toxins.

Any of the immunoassays described above can be used to analyze a tissue sample from a patient. Spectrin breakdown products have been detected in a number of tissues (see above). A preferred biological sample for diagnosis of neurodegenerative conditions is CSF, as it would contain spectrin BDPs specifically generated from a degenerative condition of the nervous system. Lumbar CSF can be obtained from patients by standard methods (The Merck Manual 12th edn., D. N. Holvey, Ed., Merck Sharp and Dohne Research Labs Publishing, New Jersey, 1972. pp. 1746–1748). Other preferred biological samples for this analysis include amniotic fluid, blood, and components of blood, which can be obtained by standard methods.

The levels of calpain-generated spectrin BDPs in the above-described biological samples can be determined in any of the immunoassays described above employing spectrin BDP-specific antibodies. The level of spectrin breakdown products detected in the biological sample from the subject being analyzed is compared to the level in an unaffected patient, or to a known standard. An increase in calpain-generated spectrin BDPs of preferably 50 percent, and more preferably 150 percent, compared to control samples is considered diagnostic for a neurodegenerative condition.

The above-described diagnostic assays can be facilitated by the use of kits which contain the reagents required for carrying out the assays.

Inhibitors

Detection of increased levels of calpain-generated spectrin BDPs has been associated with the occurrence of several neurodegenerative conditions (see above). Thus, administering a compound which decreases the level of calpain activation may be useful for treating these conditions.

Several classes of calpain inhibitors have been identified and found to provide protection against a variety of neurodegenerative diseases and conditions (Bartus et al., WO 92/11850). The method used by Bartus et al. to identify compounds that inhibit cleavage of spectrin requires samples to be fractionated by gel electrophoresis in order to separate spectrin BDPs from intact spectrin. As described above, gel electrophoresis followed by Western blotting is very time consuming, cumbersome, expensive, and requires a high level of skill.

The antibodies of the present invention recognize spectrin BDPs generated by activated calpain, but not intact spectrin, or the spectrin BDPs produced by other proteases. Thus, these antibodies can be used in relatively simple, inexpensive, and rapid immunoassays, such as an ELISA, as sample fractionation is not required for these antibodies to distinguish spectrin BDPs from intact spectrin. The antibodies of the invention can be used in methods, such as ELISAs, for identifying calpain inhibitors. Because of its relative simplicity and specificity for activated calpain, the use of the antibodies of the invention in an ELISA provides a significant advance over previous methods for identifying calpain inhibitors.

Small organic molecules are desirable candidate inhibitor compounds as frequently these molecules are capable of passing through the plasma membrane. The screening for calpain inhibitors is carried out as follows. First, compounds are subjected to a biochemical screen. Second, compounds which test positive in the biochemical screen are tested in cultured cells or tissue extracts. Finally, compounds which test positive in the cultured cells or tissue extracts are tested in an animal model system.

In the biochemical screen, purified spectrin (Davis et al., supra) is incubated with calpain (~3 $\mu$g/ml; purified by the method of Seubert et al., 1987, supra) under appropriate conditions (100 $\mu$M $CaCl_2$, 20 mM Tris-HCl (pH 7.5), 5 mM BME, 150 mM NaCl, at 30° C.) in the presence and absence of the candidate compound. The level of spectrin BDPs is determined by using any of the spectrin BDP-specific antibodies of the invention in any of the immunoassays described above, e.g., an ELISA. A compound tests positive if the amount of spectrin BDPs present in the sample containing the inhibitor is less than that present in the sample lacking the inhibitor.

Compounds which test positive in the biochemical assay are subsequently analyzed in cultured or freshly isolated cells, such as platelets (isolated by standard methods, see, e.g., Ferrell et al., J. Biol. Chem. 264:20723–20729, 1989), which express calpain and spectrin, and have a membrane that has many similarities to that which constitutes the blood brain barrier. The cells may be cultured in the presence of a candidate compound and a calcium ionophore, such as A23187, which provides sufficient intracellular calcium to activate calpain. Levels of calpain-generated spectrin BDPs formed are determined in an immunoassay using spectrin BDP-specific antibodies, as described above. A compound tests positive if the amount of spectrin BDPs present in the sample containing the inhibitor is less than that present in the sample lacking the inhibitor.

Other cells that can be used in methods for identifying calpain inhibitors include cells such as N18-RE105 cells which are neuroblastoma-retinal hybrids that experience calcium dependent cytotoxicity in the presence of glutamate. Thus, these cells serve as an in vitro model for neuropathology. Molt-4 leukemic cells (see below) or crude brain extracts may also be used in the screening methods of the invention (brain tissue is homogenized in 10 mM Tris-HCl pH 7.4, 0.32M sucrose, 1 mM EGTA, 1 mM dithiothreitol on ice; cellular debris and nuclei are removed by low speed centrifugation).

Compounds found to decrease calpain activation levels in the cell culture assay are further tested in animal model systems. A candidate compound is administered to an animal, e.g. a gerbil, mouse, or rat, and the effect of the compound on calpain activation is determined by monitoring the levels of calpain-generated spectrin BDPs in the animal by an immunoassay, such as an ELISA, employing any of the spectrin BDP-specific antibodies of the invention. Tissues of the animal that can be analyzed for spectrin BDPs include, but are not limited to blood, CSF, brain slices, and brain homogenates.

Use of Inhibitors

The invention provides methods for identifying inhibitors of calpain activation. Calpain activation and elevated levels of spectrin BDPs have been associated with a number of pathological diseases including Alzheimer's Disease, Parkinson's Disease, muscular dystrophy, multiple infarction dementia, intraventricular hemorrhage, Pick's disease, subarachnoid hemorrhage, HIV-induced neuropathy, stroke, and retinal disease, as well as non-pathological cellular insults which affect the nervous system including trauma, hypoxia, anoxia, ischemia, head trauma, spine trauma, lesions, and exposure to toxins. Thus, the inhibitors of the invention can be used in methods to prevent or treat these conditions.

The inhibitors can be administered to the patient by any appropriate method suitable for the particular inhibitor, e.g., orally, intravenously, parenterally, transdermally, or transmucosally. Therapeutic doses are determined specifically for each inhibitor, most being administered within the range of 0.001–100.0 mg/kg body weight, or within a range that is clinically determined as appropriate by those skilled in the art.

The following examples are meant to illustrate, but not limit, the methods and compositions of the present invention. Other suitable modifications and adaptations of the variety of conditions and parameters normally encountered in immunodiagnostics which are obvious to those skilled in the art are within the spirit and scope of the present invention.

EXAMPLES

Example 1
Production and Characterization of Antibodies that Specifically React with Calpain-Generated Spectrin Breakdown Products Antibodies were raised against short peptides corresponding to the COOH-terminus of the $NH_2$-terminal alpha-spectrin fragment (CQQQEVY; SEQ ID NO: 1) generated by calpain cleavage, and the $NH_2$-terminus of the COOH-terminal alpha-spectrin fragment (GMMPRDGC; SEQ ID NO: 2) generated by calpain cleavage (FIG. 1; the peptides (CQQQEVY (SEQ ID NO: 1) and GMMPRDGC (SEQ ID NO: 2)) were synthesized by solid phase methods and their structures confirmed by fast atom bombardment-mass spectrometry. Each peptide was conjugated through its cysteine residue to keyhole limpet hemocyanin with the heterobifunctional coupling agent maleimidobenzoyl-N-hydroxysuccinimide ester (Calbiochem, San Diego, Calif.), and then the conjugates were used to immunize rabbits (Harlow et al., supra). Antibodies 37 and 38 were directed against CQQQEVY (SEQ ID NO: 1), while antibody 39 was prepared using GMMPRDGC (SEQ ID NO: 2)).

Figure 1:
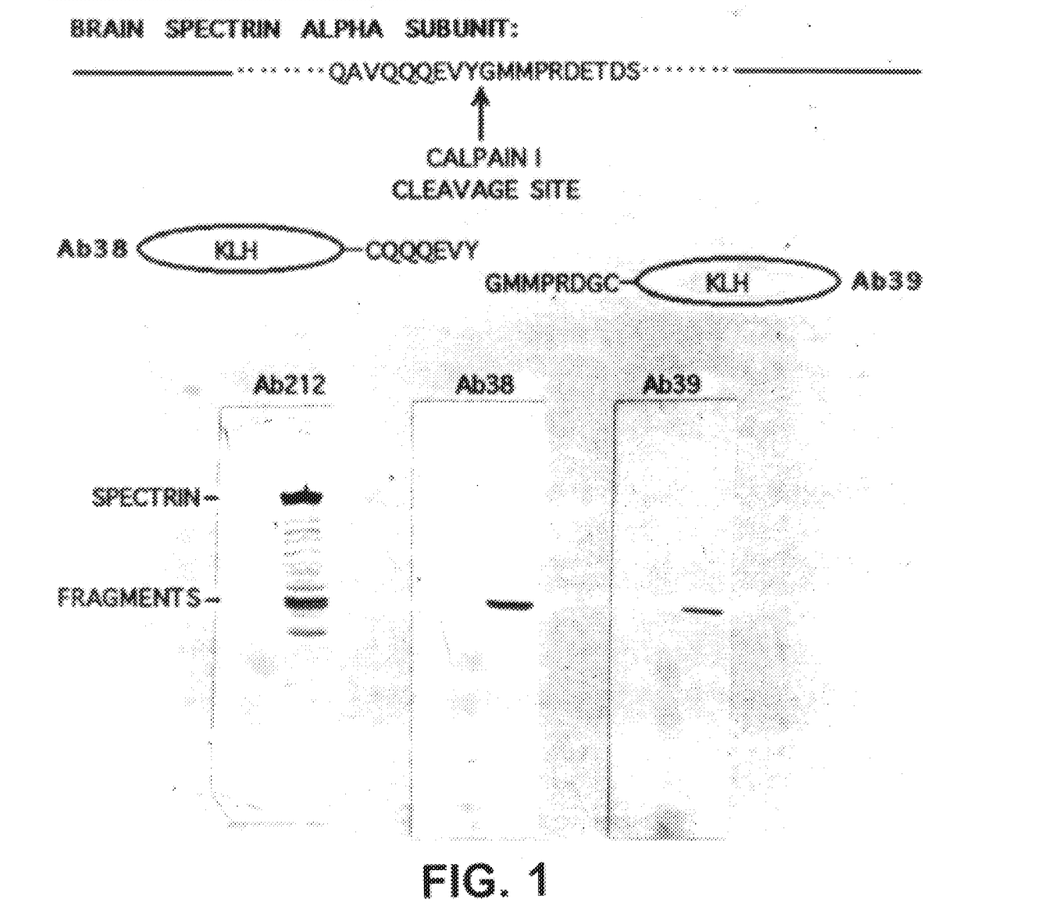
FIG. 1 is a representation of the calpain I cleavage site in the alpha subunit of brain spectrin and the keyhole limpet hemocyanin (KLH)-peptide conjugates to which Abs 38 and 39 were raised. Also shown is an immunoblot of post-ischemic gerbil hippocampal membranes probed with Abs 212, 38, and 39. Intact spectrin and spectrin breakdown products are indicated.

The reactivity of antibodies 37, 38, 39, and 212 (Ab212 was prepared against purified rat spectrin as described previously; Siman et al., 1988, supra; Siman et al., 1989, supra) was assessed by immunoblot analysis of hippocampal membranes prepared from gerbil brain 2 days following transient global ischemia (FIG. 1). This insult has previously been shown to elicit an increase in spectrin degradation in the hippocampus (Seubert et al., 1989, supra; Lee et al., supra). Anti-CQQQEVY (Abs 37 and 38) and anti-GMMPRDGC (Ab39) labeled 150 kDa polypeptides which were confirmed as being spectrin BDPs by their immunoreactivity with Ab212 (FIG. 1). Unlike Ab212, however, the anti-peptide antibodies (Abs 37, 38, and 39) exhibited little or no reactivity with intact alpha-spectrin. These results show that the epitopes recognized by the anti-peptide antibodies (Abs 37, 38, and 39) are inaccessible in intact spectrin, but become exposed upon the proteolytic degradation of spectrin evoked by cerebral ischemia.

Example 2
Calpain I is Activated in situ by Cerebral Ischemia

Figure 2:
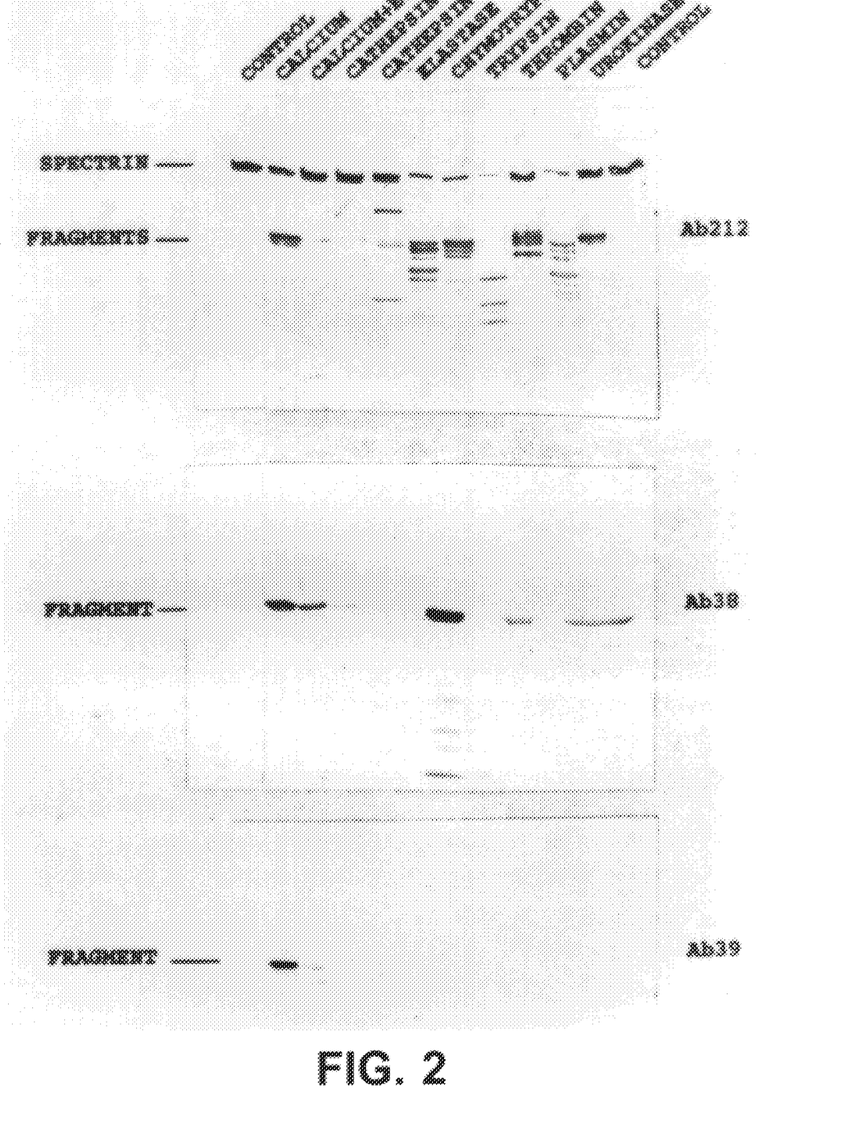
FIG. 2 is an immunoblot of gerbil hippocampal membranes treated under the conditions indicated and probed with Abs 212, 38, and 39. Intact spectrin and spectrin breakdown products are indicated.

Because calpain I is known to cleave brain spectrin in the domain used to generate the anti-peptide antibodies, it is a candidate for the hippocampal protease activated in situ by cerebral ischemia. To investigate this possibility, the ability of calpain and eight other proteases to cleave spectrin and form proteolytic fragments that are reactive with Ab38 and Ab39 was determined by immunoblot analysis. Gerbil brain membranes were either treated with calcium to activate the endogenous calpain (Baudry et al., Science 212:937–938, 1981; Siman et al., J. Neurochem. 41:950–956, 1983) or with the eight other mammalian proteases (FIG. 2). A crude membrane fraction was prepared from gerbil brain by homogenization in 10 volumes 50 mM Tris-HCl (pH 7.4)/4 mM EDTA at 4° C. Following centrifugation at 500×g for 5 minutes, the pellet was discarded and the supernatant was centrifuged at 30,000×g for 20 minutes. The pellet was taken as the crude membrane fraction. Membranes were washed with one of four buffers: (I) 50 mM Tris-HCl (pH 7.4); (II) I+10 mM $CaCl_2$; (III) 50 mM sodium acetate (pH 6.0)/1 mM EDTA/5 mM βME; (IV) II+5 mM βME. Membranes (50 μl) were incubated with the following proteases (obtained from Sigma, St. Louis, Mo. or Boehringer Mannheim, Indianapolis, Ind.) for 1 hour at 37° C.: human cathepsin B (50 mU) or cathepsin L (1.25 mU) in buffer III; human neutrophil elastase (250 ng), bovine α-chymotrypsin (50 ng), bovine trypsin (100 ng; tosylphenylalanine-chloromethylketone (TPCK)-treated), human plasmin (10 mU), or human kidney urokinase (60 mU) in buffer I; human thrombin (0.4 U)+200 μM E64 in buffer II. In addition, endogenous calpain (Baudry et al., supra; Siman et al., 1983, supra) was activated by incubation in buffer IV. Reactions were stopped by the addition of SDS-PAGE sample buffer, followed by boiling. Samples were fractionated on 5% SDS-PAGE gels, which were transferred to nitrocellulose, and immunostained (Siman et al., 1988, supra; Siman et al., 1989, supra) with either Ab212 (1:800), Ab38 (1:500), or Ab39 (1:300).

The antibody to brain spectrin (Ab212) labeled the intact >240 kDa alpha-subunit as well as a number of smaller breakdown products generated by many of the proteases. Addition of calcium, cathepsin L, elastase, chymotrypsin, trypsin, thrombin, plasmin, and urokinase all led to spectrin cleavage and production of Ab212-immunoreactive fragments. The effect of calcium was blocked by the cysteine protease inhibitor E64, consistent with the activation of calpain. In contrast, Abs 38 and 39 bound two independent polypeptides of approximately 150 kDa generated only by calcium treatment and, in the case of the former antibody, by chymotrypsin. Thus in vitro activation of calpain, but not eight other mammalian proteases, generated polypeptide fragments similar to those generated in vivo by the ischemia-activated hippocampal protease. The polypeptides labeled by Abs 38 and 39 represent the two halves of calpain-cleaved alpha-spectrin.

Figure 3:
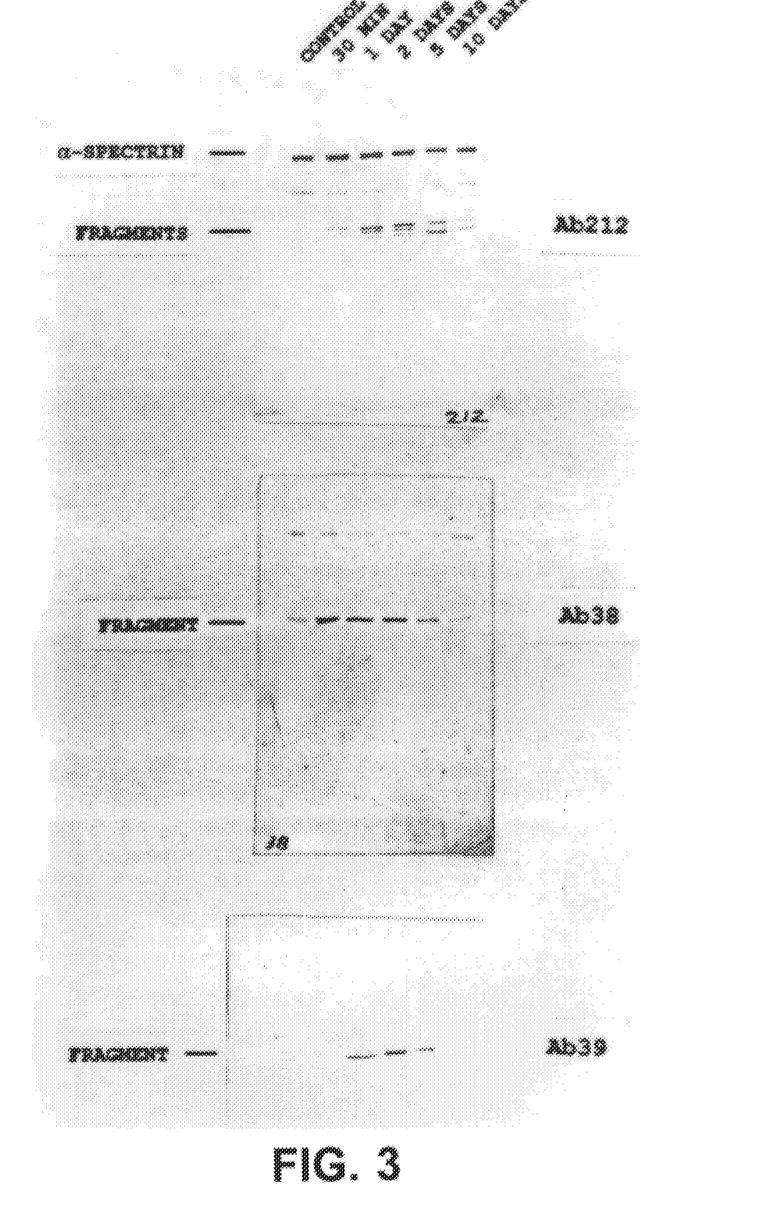
FIG. 3 is an immunoblot of gerbil hippocampal membranes prepared at the indicated times following a 5 minute bilateral occlusion of the carotid arteries and probed with Abs 212, 38, and 39.

Example 3
Time Course of Calpain Activation of Following Transient Cerebral Ischemia Immunoblot analysis using Ab212 revealed that spectrin BDPs were present in the hippocampus as early as 30 minutes following a 5 minute bilateral occlusion of the carotid arteries (FIG. 3; ischemic Surgery: male Mongolian gerbils weighing 50–80 g (Tumblebrook Farms, West Brookfield, Mass.) were anesthetized with Nembutal (50 mg/kg i.p.). An anterior ventral midline incision was made in the neck, right and left common carotid arteries were isolated from the vagus nerve, and suture thread was tied around each artery to achieve total occlusion of blood flow for a period of 1, 5, or 10 minutes. Control animals were anesthetized, but were not subjected to the carotid occlusion. At the end of the ischemic period, the suture threads were removed, and the incision was closed with wound clips after ascertaining that blood flow was completely restored to both carotid arteries. Body temperature was monitored with a rectal probe and maintained within normal physiological limits by the use of a heat lamp throughout the surgery and an incubator during the post-operative recovery period. After the surgery, the gerbils were anesthetized and killed at 30 minutes, or 1, 2, 5, or 10 days following ischemia. Animals to be processed for Western blot analyses were decapitated and the dorsal hippocampus homogenized; those animals to be processed for silver staining or immunocytochemistry (see below) were perfused transcardially and the brains were prepared as described below. Three gerbils were used for each experimental condition).

The magnitude of ischemia-induced spectrin degradation in the hippocampus peaked at 1 to 2 days, and was minimal by 10 days following the carotid occlusion. To further investigate the identity of the hippocampal protease(s) activated at the various time points by transient ischemia, the same samples were immunolabeled with Abs 38 and 39, which are selective for calpain-generated spectrin derivatives. Like Ab212, these Abs labeled 150 kDa spectrin fragments which were present in ischemic hippocampus and barely detectable in control hippocampus, but unlike Ab212, did not label intact spectrin subunits (>240 kDa). Levels of the fragments were increased at 30 minutes, remained elevated for the next two days, and then declined, in general agreement with the pattern exhibited by the Ab212-reactive spectrin derivatives.

Example 4
Localization of Calpain Activation Following Transient Cerebral Ischemia The antibodies reactive with calpain-derived fragments of brain spectrin were used as neuroanatomical tools to localize calpain activation following cerebral ischemia. The pattern of immunohistochemical staining in sagittal sections of the gerbil brain for calpain-generated spectrin fragments was determined at 30 minutes, and 1, 2 and 10 days following ischemia (FIG. 4; histology: the indirect immunoperoxidase histochemical procedure used to localize calpain-generated fragments of brain spectrin has been described previously (Siman et al., Neuron 3:275–285, 1989). Briefly, at various times after ischemia, gerbils were deeply anesthetized with nembutal and perfused with 0.1M sodium phosphate buffer (pH 7.4) followed by 4% paraformaldehyde in phosphate buffer. Brains were post-fixed in paraformaldehyde and cryo-protected overnight in 20% sucrose in 0.1M sodium phosphate at 4° C. Sagittal sections were prepared from frozen brains at 45 μm and incubated in 50% methanol containing 1% $H_2O_2$ for 30 minutes. After rinses in 10 mM Tris-HCl/150 mM NaCl (pH 7.4; TBS), sections were incubated for 30 minutes in 5% horse serum in TBS with 0.1% Triton X-100, then with Ab37 (1:10,000) overnight at 4° C. After washes, sections were incubated with goat anti-rabbit IgG (Cappel; 1:100), followed by a rabbit peroxidase/anti-peroxidase complex (Cappel; 1:500). Diaminobenzidine (500 μg/ml) and $H_2O_2$ (0.0015%) in TBS were used for color development. For pre-absorption, 50 μg of peptide immunogen (CQQQEVY; SEQ ID NO: 1) was combined with 1 ml of Ab37 (1:10,000) and incubated for 1 hour at room temperature. This primary antibody solution was then used as above. Additional control sections were handled as above, except for the absence of primary antibody).

Figure 4A:
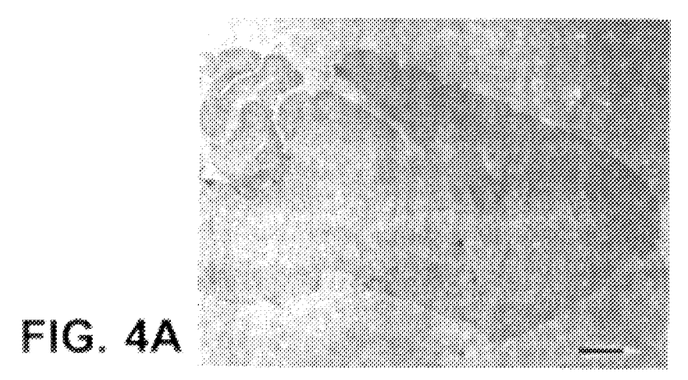
Figure 4B:
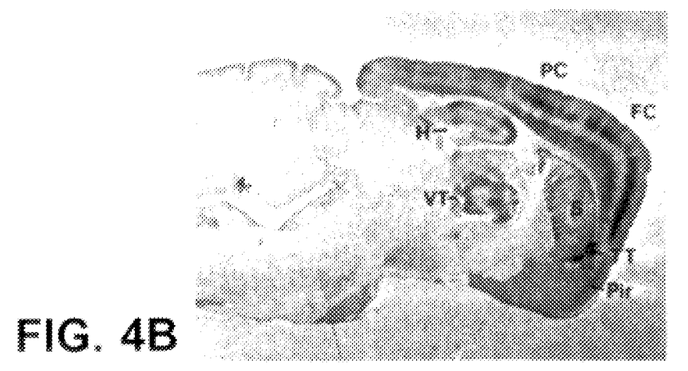
Figure 5A:
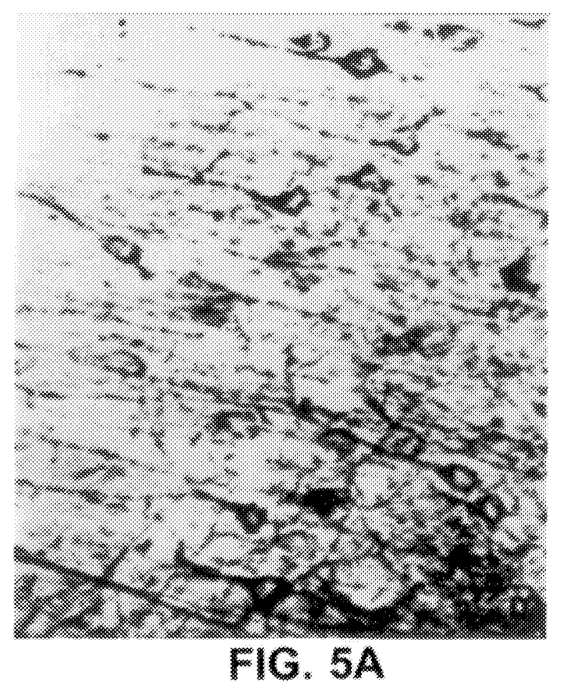
Figure 5B:
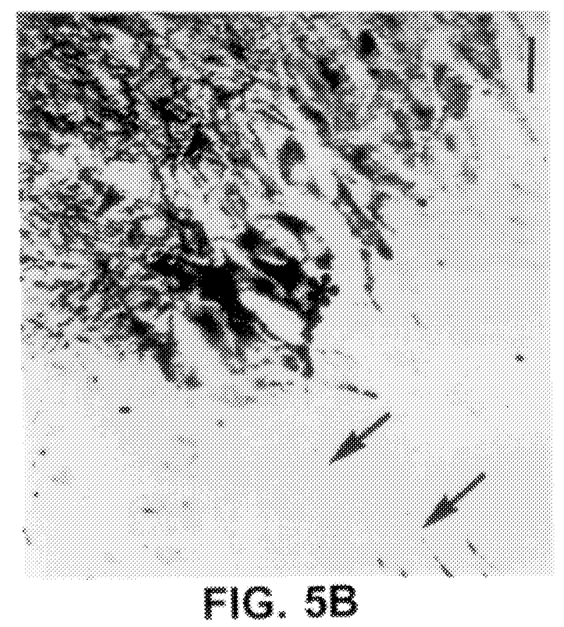

Brain sections from control (non-ischemic) animals exhibited only very light immunostaining of neuronal perikarya with Ab38 (FIG. 4A), whereas by 30 minutes following a 5 minute bilateral occlusion of the carotid arteries, intense immunoreactivity was apparent in the parietal and frontal cortex (layers I, III and V), piriform cortex, tenia tecta, striatum, ventral thalamus and hippocampus (FIG. 4B). Hippocampal immunoreactivity at this time point was primarily confined to the CA3 sector, with some staining of neurons in the posterior CA1 subfield and at the CA2–CA3 border. The dentate gyrus was unstained. Immunoreactivity for calpain-degraded spectrin was neuron-specific, and present in perikarya as well as basal and apical dendrites of hippocampal neurons (FIGS. 4F and 5; see also FIG. 7, below) and the long primary dendrites of neocortical pyramidal neurons (FIG. 5).

Figure 4C:
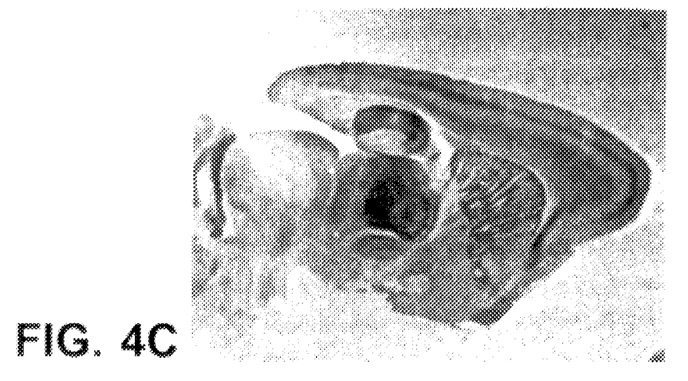
Figure 4D:
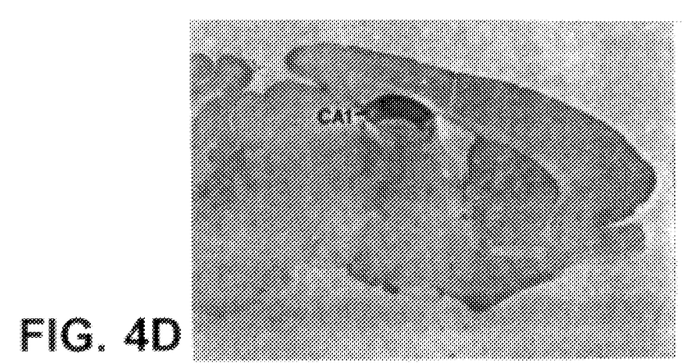
Figure 4E:
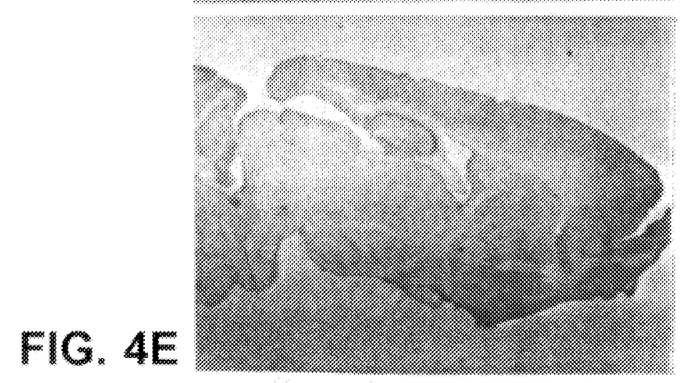
Figure 4F:
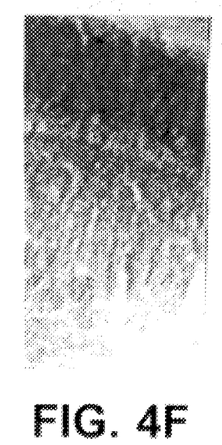
Figure 4G:
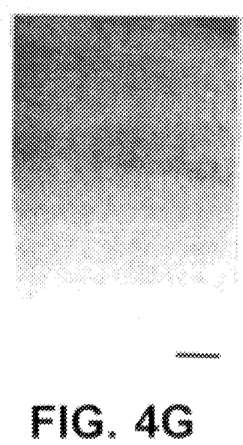

At 24 hours following ischemia, cortical, thalamic and striatal immunostaining was still present, but the hippocampal staining was more intense, with a broader distribution of immunoreactivity in the CA1 region (FIG. 4C). At this time, staining of apical and basal dendrites of pyramidal neurons in area CA1 became prominent. By 2 days following the 5 minute ischemic insult, only the CA1 region of the hippocampus was intensely stained; the CA3 subfield of the hippocampus, the cortex, thalamus and striatum no longer exhibited significant immunoreactivity for calpain-degraded spectrin (FIG. 4D). By 10 days following ischemia, virtually all immunoreactivity had disappeared, and sections from ischemic brain were indistinguishable from those from control brain (FIG. 4E).

Pre-absorption of Ab38 with an excess of the peptide immunogen totally blocked immunostaining of the tissue sections (FIG. 4G vs. FIG. 4F), consistent with specific labeling of calpain-degraded spectrin epitopes.

Example 5
Activation of Calpain Following Short or Long Duration of Ischemia

Figure 6A:
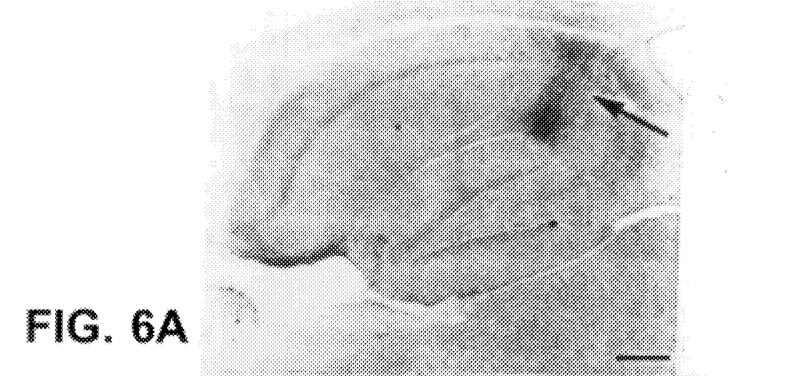

In order to differentiate between the effects of non-damaging versus severely damaging periods of ischemia on calpain activation, we compared the results of a short (one minute), intermediate (five minute), or long (ten minute) interruption of blood flow. One minute occlusion of the carotid arteries, which does not lead to neuronal degeneration, resulted in the appearance of a narrow band of Ab38-immunoreactive neurons in the CA2–CA3 border region of the hippocampus by 30 minutes post-occlusion (FIG. 6A). There was not any other immunoreactivity apparent at 30 minutes, and by 3 days following carotid occlusion the brain was devoid of immunoreactivity to Ab38.

Figure 6B:
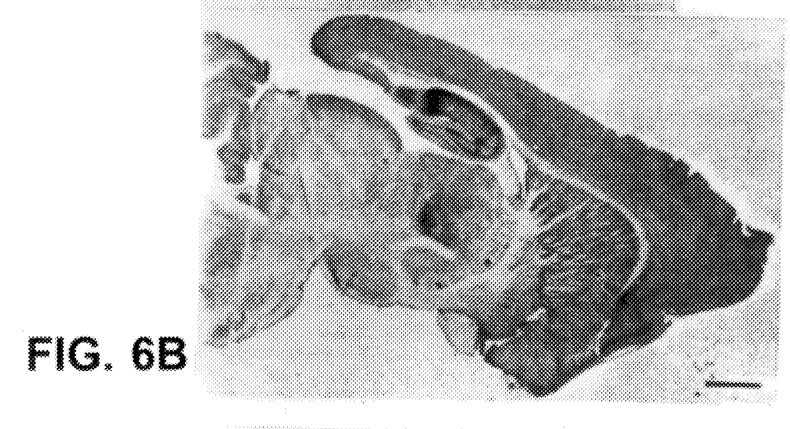
Figure 6C:
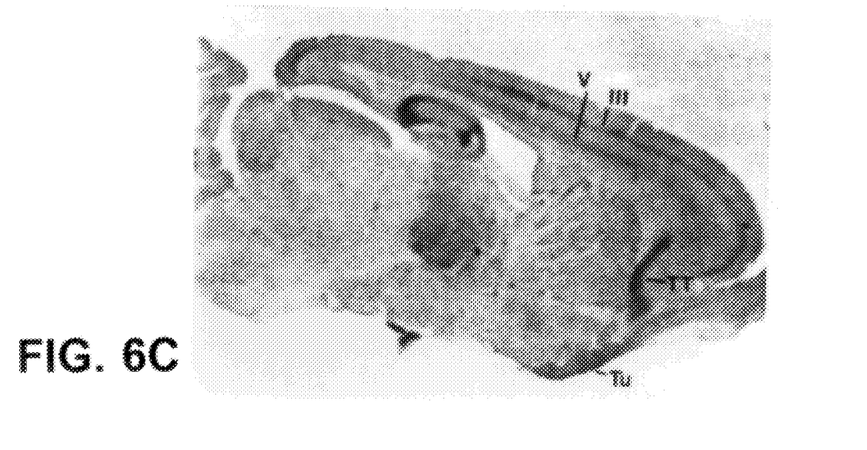

In contrast, a ten minute occlusion of the carotid arteries produced a pattern of staining in the hippocampus (CA1 and CA2–CA3 border zone), cortex, tenia tecta, and thalamus which was manifested at 30 minutes and persisted for 3 days following the ischemic insult (FIG. 6C). Some cases also exhibited prominent immunoreactivity in the striatum and olfactory tubercle. The immunoreactivity at 3 days following an intermediate (5 minute) ischemic insult in the cerebral cortex, tenia tecta, and thalamus was either less robust or, more commonly, completely absent. Thus, a short ischemic episode produced no prolonged calpain activation, whereas an intermediate episode led to calpain activation confined to hippocampal area CA1, and a long episode induced calpain activation that extended outside of hippocampus and included regions of cerebral cortex and striatum.

Figure 6D:
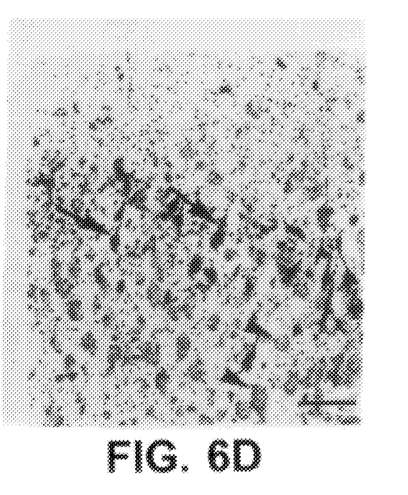
FIGS. 6D and 6E are representative photographs of silver impregnation histochemistry analysis of (FIG. 6D) CA1 region of hippocampus after 5 minutes of ischemia, 3 days post-insult, and (FIG. 6E) CA2/3 border region of hippocampus after 5 minutes of ischemia, 3 days post-insult. Arrowheads indicate healthy neuronal cell bodies, while the arrows denote degenerating neurons. Scale bars are 200 $\mu$m (FIG. 6A), 1 mm (FIGS. 6B–6C), 25 $\mu$m (FIG. 6D), and 50 $\mu$m (FIG. 6E).
Figure 6E:
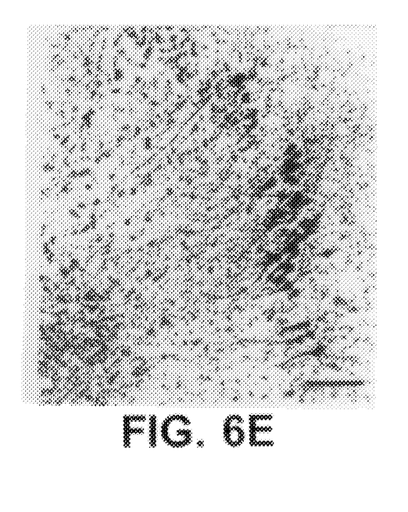

Silver impregnation histochemistry performed 3 days after a five minute ischemic insult demonstrated degeneration of neurons in the CA1 and CA2–CA3 border regions of the hippocampus (FIG. 6D and E; silver staining for degenerating neurons was performed by a modified Gallyas method, as described previously (Nadler et al., Meth. Enzymol. 103:393–400, 1983; Siman et al., Neuron, 1989, supra)). This pattern of silver staining corresponded with the pattern of intense hippocampal immunoreactivity for calpain-degraded spectrin seen under the same conditions of ischemia (FIG. 6B).

Example 6

Attenuation of Ischemia-Induced Calpain Activation with MK-801

Figure 7A:
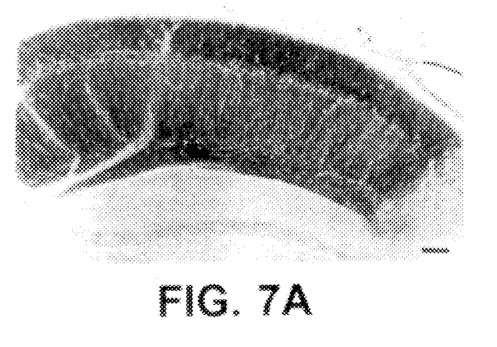
Figure 7B:
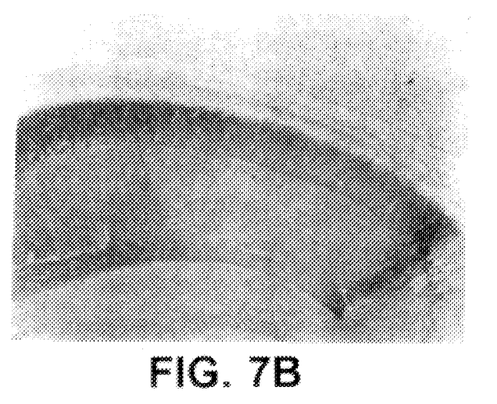
Figure 7C:
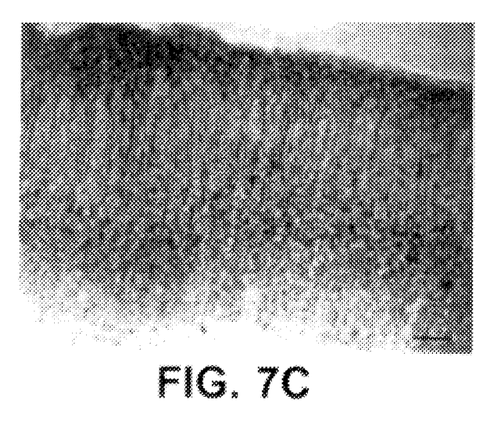
Figure 7D:
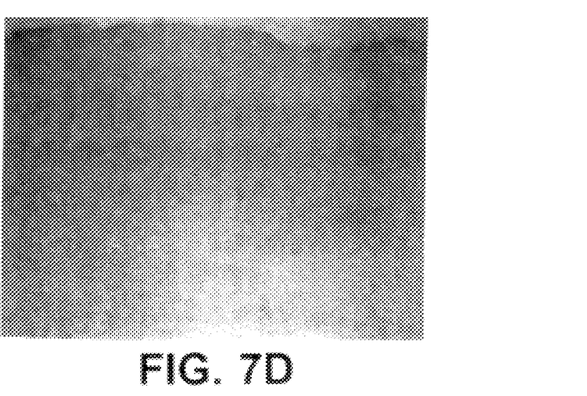
Figure 7E:
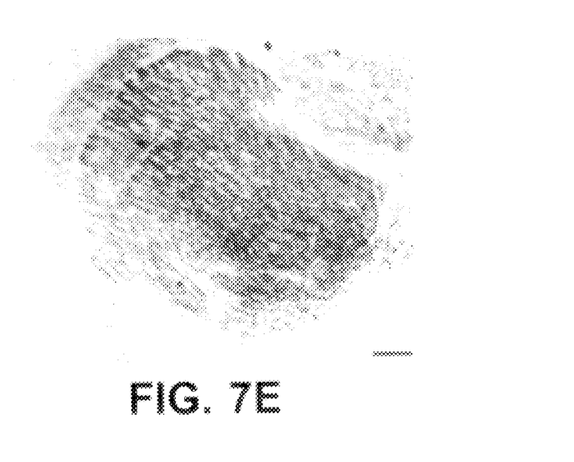

To begin to define the receptor-based mechanism by which calpain activation and spectrin degradation are triggered, gerbils were treated with the non-competitive NMDA receptor antagonist, MK-801, immediately following a 5 minute occlusion of the carotid arteries. Treatment of gerbils with a dose of MK-801 (3 mg/kg, i.p.) that partially blocks hippocampal neuronal death (Roberts-Lewis et al., Ann. N.Y. Acad. Sci. 679:78–86, 1993) resulted in a partial attenuation of immunoreactivity for calpain-degraded spectrin in the CA1 region of hippocampus 2 days following ischemia (FIG. 7A vs. FIG. 7B). Thus, a treatment that reduces ischemia-induced hippocampal neurodegeneration results in a parallel decrease in calpain activation and spectrin degradation. At 1 day following the ischemia, MK-801 treatment produced an essentially complete blockade of immunostaining in the cortex (FIG. 7C vs. FIG. 7D), thalamus and striatum, suggesting that the rapid and more widespread calpain-mediated spectrin degradation results primarily from activation of NMDA receptors.

Example 7

Filter-binding ELISA for Calpain-Generated Spectrin Breakdown Products

Figure 8A:
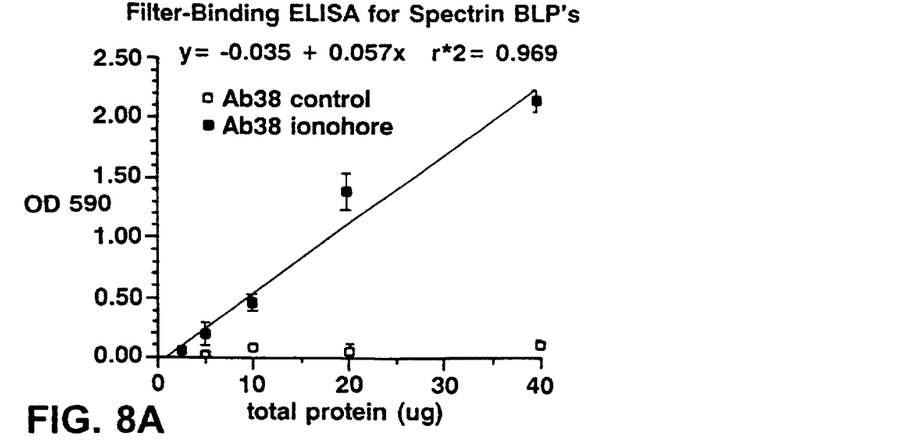
FIG. 8 is a series of graphs showing the results of filter binding ELISAs for calpain-generated spectrin BDPs carried out in the presence (ionophore) and absence (control) of calcium ionophore A23187.
Figure 8B:
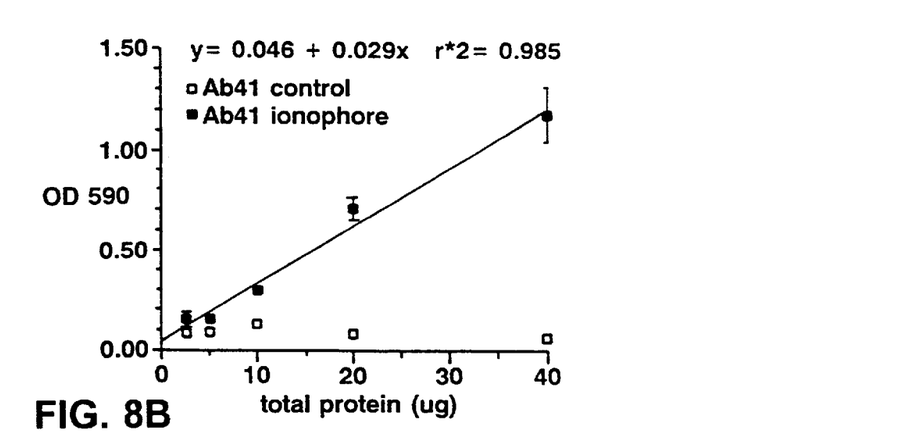
Figure 8C:
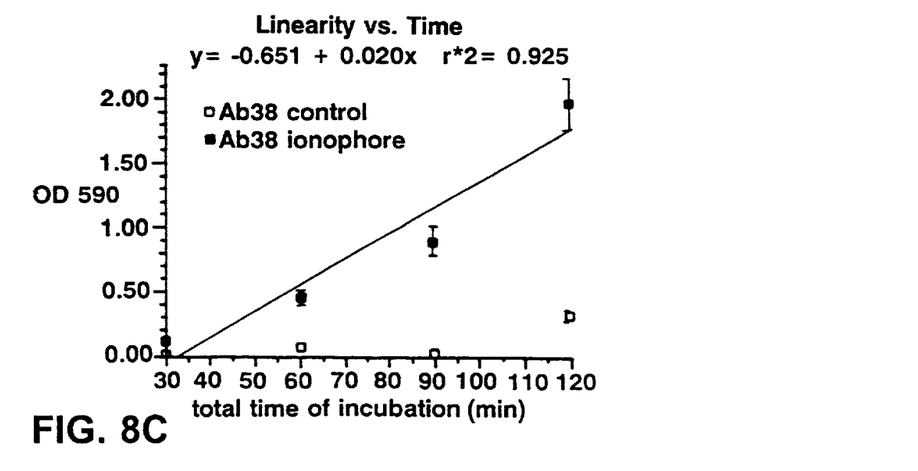

Molt-4 leukemic cells (National Institute of General Medical Sciences, Human Genetic Mutant Cell Repository, Camden, N.J., (HGMCR), Repository number: GM2219C) were treated in the absence (FIG. 8; control) or presence of 20 µM calcium ionophore, A23187 (Molecular Probes, Inc., Eugene, Oreg.), and 5 mM calcium chloride in Hepes buffered saline (FIG. 8; ionophore). These experimental conditions allow influxes of calcium into the cells, activating calpain, followed by subsequent calpain-mediated degradation of spectrin. Following a 60 minute incubation, detergent cell lysates were prepared by incubating cells with 20 mM Tris-HCl/150 mM NaCl/1% Nonidet 40 (NP40)/10 mM EDTA pH 7.5. Nuclei were removed by centrifugation. Following addition of SDS to a final concentration of 0.2% and heating to 95° C., the total lysate protein concentration was determined by the BCA method (Pierce, Inc.). Ethanol was then added to cell lysates (20 µg total protein load, unless stated otherwise) prior to application to nitrocellulose-bottom 96 well filtration plates (Millipore, Inc., Bedford, Mass.). For ELISA analysis, wells were subsequently incubated for 1 hour at room temperature with Ab38, Ab41, or both, diluted in block buffer (block buffer=5% Carnation instant milk in TBST (20 mM Tris-HCl/0.15M NaCl/0.05% Tween 20 pH 7.5)). Wells were washed 5 times with 200 µl TBST and incubated with a dilution of alkaline phosphatase-conjugated goat anti-rabbit IgG (BioRad Labs) diluted in block buffer. Following a 1 hour incubation, the wells were washed 5 times with 200 µl 20 mM Tris-HCl/0.5M NaCl/0.05% Tween 20 pH 7.5, and 2 times with 20 mM Tris-HCl/0.15M NaCl pH 7.5. For detection of bound antibodies, the ELISA amplification system (Gibco BRL, Gaithersburg, Md.) was utilized. Wells were incubated for 60 minutes with the substrate, followed by a 60 minute incubation with the amplification reagents. Dilutions of substrate and amplifier were as recommended by the manufacturer. Signal was measured at OD490. As illustrated in FIG. 8, the signal was linear with respect to time and protein concentration. Most significantly, the signal was detected only in lysates of cells which had been treated with calcium ionophore to induce calpain activation and subsequent spectrin degradation.

Other Embodiments

The above examples are, therefore, to be construed as merely illustrative, and not limitative of the remainder of the disclosure in any way whatsoever.

From the above description, one skilled in the art can easily ascertain the essential characteristics of the present invention, and without departing from the spirit and the scope thereof, can make various changes and modifications of the invention to adapt it to various usages and conditions. All publications cited herein are fully incorporated by reference in their entirety.

What is claimed is:

1. A method for measuring the ability of a candidate compound to decrease calpain activity, said method comprising the steps of:
   (a) forming a sample by incubating spectrin, calpain and said candidate compound together under conditions in which calpain is activated;
   (b) contacting said sample with a first antibody that does not specifically bind intact spectrin and specifically binds to a peptide having the amino acid sequence of SEQ ID. NO: 1 or a second antibody that does not bind specifically to intact spectrin and specifically binds to a peptide having the amino acid sequence of SEQ ID. NO: 2; and
   (c) determining the level of said antibody bound to said sample, wherein a level of less than a control sample without said compound indicates that the compound decreases calpain activity.

2. A method of measuring the ability of a candidate compound to decrease calpain activity, said method comprising the steps of:
   (a) providing a cell culture that expresses calpain and spectrin;
   (b) activating calpain in said cell culture in the presence of said candidate compound;
   (c) contacting said culture with a first antibody that does not specifically bind intact spectrin and specifically binds to a peptide having the amino acid sequence of SEQ ID. NO: 1 or a second antibody that does not bind specifically to intact spectrin and specifically binds to a peptide having the amino acid sequence of SEQ ID. NO: 2; and
   (d) determining the level of said antibody bound to said culture, wherein a level of less than a control culture without said compound indicates that the compound decreases calpain activity.

3. A method of measuring the ability of a candidate compound to decrease calpain activity, said method comprising the steps of:
   (a) administering said compound to a mammal;
   (b) activating calpain in said mammal;
   (c) obtaining a biological sample from said mammal;
   (d) contacting said sample with a first antibody that does not specifically bind intact spectrin and specifically binds to a peptide having the amino acid sequence of SEQ ID. NO: 1 or a second antibody that does not bind specifically to intact spectrin and specifically binds to a peptide having the amino acid sequence of SEQ ID. NO: 2; and
   (e) determining the level of said antibody bound to said sample, wherein a level of less than a control sample without said compound indicates that the compound decreases calpain activity.

4. The method of claim 2, wherein said sample is selected from the group consisting of tissue and biological fluid.

5. The method of claim 4 wherein said tissue is selected from the group consisting of submandibular glands, brush border, testes, thymus, skeletal muscle, heart muscle, lung, liver, spleen, adrenal gland, kidney, blood platelets and brain.

6. The method of claim 4 wherein said biological fluid is selected from the group consisting of blood, sera, cerebral spinal fluid, and amniotic fluid.

* * * * *

UNITED STATES PATENT AND TRADEMARK OFFICE
CERTIFICATE OF CORRECTION

PATENT NO. : 5,871,712

DATED : February 16, 1999

INVENTOR(S) : Robert Siman

It is certified that error appears in the above-identified patent and that said Letters Patent is hereby corrected as shown below:

```
Cover Page, Col. 2 Other Publications Siman et al. fifth
occurrence "calpain I, and" should be --calpain I, an--.

Col. 16, line 37, "claim 2" should be --claim 3--.
```

Signed and Sealed this

Thirteenth Day of July, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 7
        ( B ) TYPE: amino acid
        ( C ) STRANDEDNESS:
        ( D ) TOPOLOGY: linear     ( x i ) SEQUENCE DESCRIPTION: SEQ ID NO: 1:

```
Cys  Gln  Gln  Gln  Glu  Val  Tyr
 1                    5
```

(2) INFORMATION FOR SEQ ID NO: 2:

(i) SEQUENCE CHARACTERISTICS:
      (A) LENGTH: 8
      (B) TYPE: amino acid
      (C) STRANDEDNESS:
      (D) TOPOLOGY: linear    (xi) SEQUENCE DESCRIPTION: SEQ ID NO: 2:

Gly Met Met Pro Arg Asp Gly Cys
1               5